(12) United States Patent
Jacobs et al.

(10) Patent No.: US 6,957,925 B1
(45) Date of Patent: Oct. 25, 2005

(54) TOOTHPASTE DISPENSING AUTOMATIC TOOTHBRUSH

(76) Inventors: Erin J. Jacobs, 86 Beaver Meadow Rd., Hogansburg, NY (US) 13655; J. Scott McDonald, 86 Beaver Meadow Rd., Hogansburg, NY (US) 13655

( * ) Notice: Subject to any disclaimer, the term of this patent is extended or adjusted under 35 U.S.C. 154(b) by 0 days.

(21) Appl. No.: 10/832,661

(22) Filed: Apr. 27, 2004

(51) Int. Cl.[7] .............................................. A46B 11/04
(52) U.S. Cl. ........................ 401/270; 401/277; 401/175
(58) Field of Search ................................ 401/270, 277, 401/171–173, 175; 15/29, 34, 35

(56) References Cited

U.S. PATENT DOCUMENTS

| | | | |
|---|---|---|---|
| 4,062,635 A | 12/1977 | Teh-Sheng | |
| 4,695,177 A | 9/1987 | Kuo | |
| 5,062,728 A | 11/1991 | Kuo | |
| 5,636,933 A | 6/1997 | Vizsolyi | |
| 5,893,378 A | 4/1999 | Llerena | |
| 5,927,889 A * | 7/1999 | La Flower | ................... 401/268 |
| 6,056,466 A | 5/2000 | Johnson et al. | |
| 6,206,600 B1 | 3/2001 | Rosenberg et al. | |
| 6,213,663 B1 | 4/2001 | Micaletti et al. | |
| 6,648,641 B1 * | 11/2003 | Viltro et al. | ................... 433/80 |
| 2005/0004498 A1 * | 1/2005 | Klupt | ......................... 601/162 |

* cited by examiner

*Primary Examiner*—Justine R. Yu
*Assistant Examiner*—Huyen Le
(74) *Attorney, Agent, or Firm*—Dale J. Ream (57) ABSTRACT

A toothpaste dispensing automatic toothbrush includes a head member mounted atop a body member with a brush head releasably coupled to the head member. A reservoir for containing toothpaste is positioned in the body member along with a pump assembly and first motor. The first motor is connected to a battery and drives the pump assembly when actuated by depression of a first switch whereby to urge toothpaste from the reservoir through a channel and onto bristles of the brush head. The brush head includes a rotor with rotor bristles that is operatively connected to a second motor. The second motor may be energized upon actuation of a second switch to cause movement of the rotor. A recharging base may be included for recharging a rechargeable toothbrush battery.

19 Claims, 7 Drawing Sheets

TOOTHPASTE DISPENSING AUTOMATIC TOOTHBRUSH

BACKGROUND OF THE INVENTION

This invention relates generally to automatic toothbrushes and, more particularly, to an automatic toothbrush that includes independent motors for dispensing toothpaste from a refillable reservoir and operating a brush head.

Electric toothbrushes have gained a high level of popularity as consumers seek a high degree of efficiency and time savings for such a routine and repetitive task. Various devices have been proposed in the art for providing automatic brush strokes which include features such as ergonomic handles, special brush configurations, and sonic brushes that break up deposits on the teeth. Although assumably effective for their intended purposes, the existing devices do not provide independently operable brush operation and refillable toothpaste dispensing operation.

Therefore, it is desirable to have an automatic toothpaste dispensing toothbrush that provides independent brush head actuation and toothpaste dispensing functionality. Further, it is desirable to have an automatic toothpaste dispensing toothbrush that may be refilled with toothpaste as needed.

SUMMARY OF THE INVENTION

Accordingly, a toothpaste dispensing automatic toothbrush according to the present invention includes a main body member defining an interior space for the positioning of several components, a head member pivotally mounted atop the body member, and a brush head releasably coupled to an upper end of the head member. A reservoir is positioned within the body member for storing a quantity of toothpaste with a channel extending through the head member and brush head for interconnecting the reservoir with apertures defined by the brush head.

A first motor is positioned in the body member and operatively connected to a pump assembly. The pump assembly is connected to the reservoir such that toothpaste may be dispensed through the brush head apertures upon user depression of a corresponding switch. A second motor is positioned in the head member and operatively coupled to the brush head. The brush head may be energized for movement upon user depression of a corresponding second switch. Therefore, the dispensing of an amount of toothpaste onto brush head bristles and operation of the brush head itself may be independently accomplished with the present invention.

A general object of this invention is to provide a toothpaste dispensing automatic toothbrush that can independently, upon actuation, dispense toothpaste and operate a brush head.

Another object of this invention is to provide a toothpaste dispensing automatic toothbrush, as aforesaid, having a pair of switches for separately and independently operating the brush head or dispensing toothpaste.

Still another object of this invention is to provide a toothpaste dispensing automatic toothbrush, as aforesaid, which includes a pump for selectively dispensing stored toothpaste between a storage reservoir and a brush head.

Yet another object of this invention is to provide a toothpaste dispensing automatic toothbrush, as aforesaid, having structure that allows viewing a level of toothpaste in the reservoir.

A further object of this invention is to provide a toothpaste dispensing automatic toothbrush, as aforesaid, that is operable with a rechargeable battery.

A still further object of this invention is to provide a toothpaste dispensing automatic toothbrush, as aforesaid, having a toothpaste reservoir that is refillable.

Other objects and advantages of this invention will become apparent from the following description taken in connection with the accompanying drawings, wherein is set forth by way of illustration and example, an embodiment of this invention.

BRIEF DESCRIPTION OF THE DRAWINGS

FIG. 6b is a sectional view taken along line 6b—6b of FIG. 6a;

DESCRIPTION OF THE PREFERRED EMBODIMENT

A toothpaste dispensing automatic toothbrush 10 according to the now preferred embodiment of the present invention will now be described in detail with reference to FIGS. 1a through 6d of the accompanying drawings.

Figure 1A:
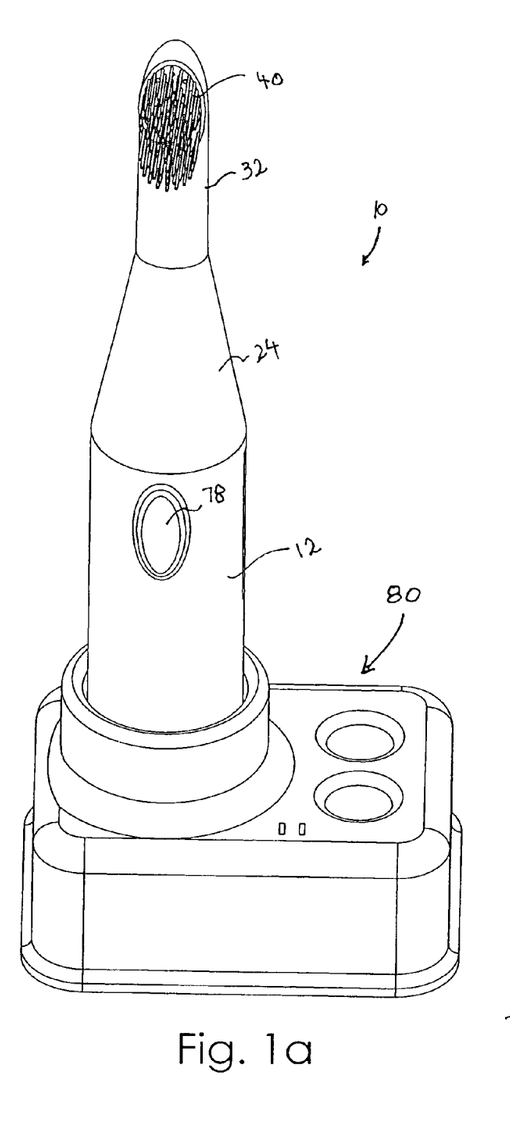
FIG. 1a is a perspective view of a toothpaste dispensing automatic toothbrush mounted in a battery recharging unit according to a preferred embodiment of the present invention.
Figure 1B:
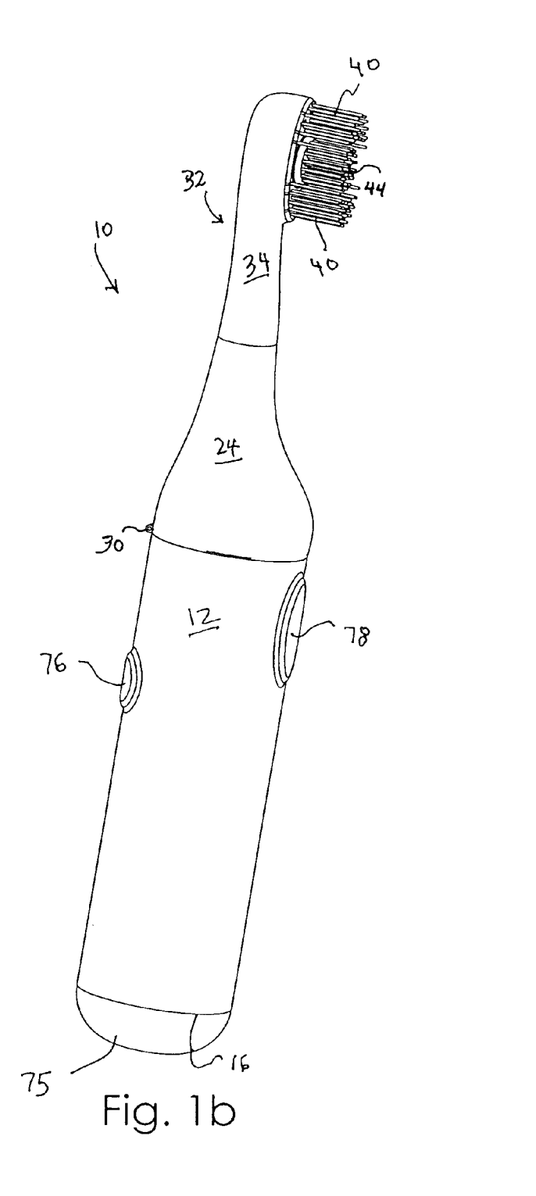
FIG. 1b is a perspective view of the toothbrush as in FIG. 1a removed from the recharging unit.

In general, the toothbrush 10 includes a main body member 12, a head member 24, and a brush head 32 releasably mounted atop the head member 24. More particularly, the body member 12 includes a generally tubular construction having an ergonomic configuration (FIG. 1). The body member 12 includes opposed first 14 and second 16 ends and is generally hollow so as to define an interior space (FIG. 2c) for holding components, as will be described in more detail later. A top wall 18 encloses the body member 12 at the first end 14 thereof (FIG. 4b).

Figure 3:
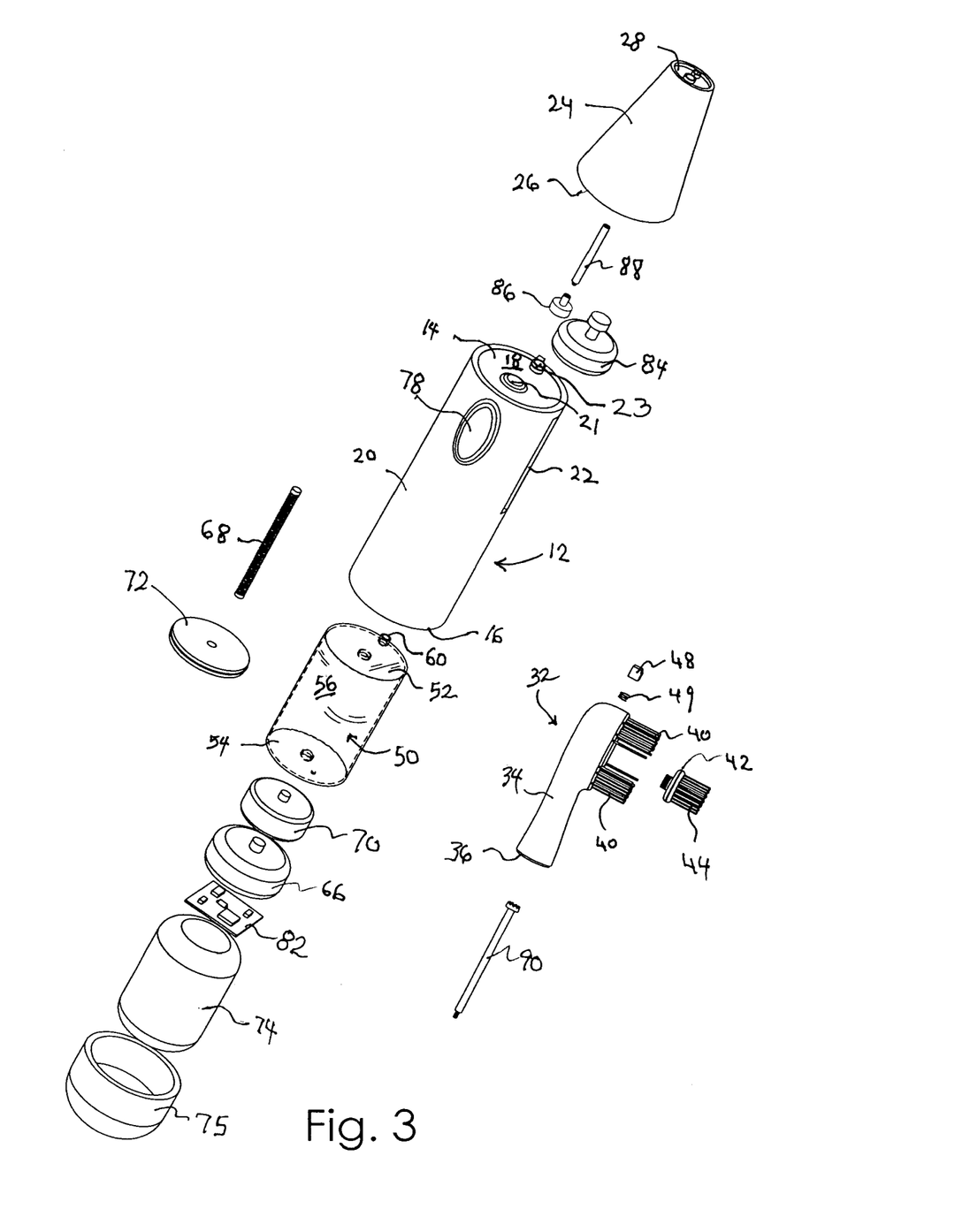
FIG. 3 is an exploded view of the toothbrush as in FIG. 1b.

The head member 24 also includes a generally tubular configuration and defines a generally hollow interior. A lower end 26 of the head member 24 is pivotally coupled to the first end 14 of the body member with a hinge 30 so as to be selectively movable between open (FIGS. 4a and 4b) and closed (FIG. 1b) configurations. The head member 24 preferably includes a frustoconical configuration in which the lower end 26 thereof presents a diameter larger than an upper end 28 thereof (FIG. 3).

Figure 2A:
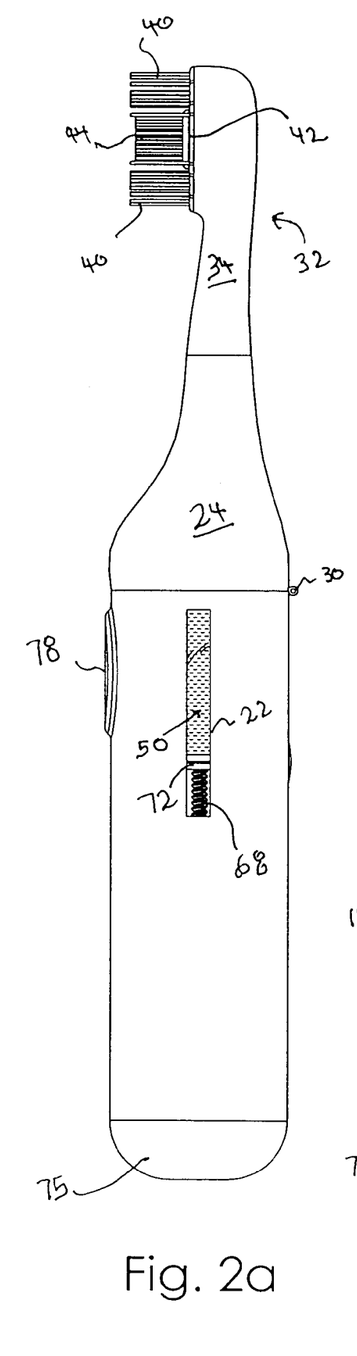
FIG. 2a is a side view of the toothbrush as in FIG. 1b.
Figures 2B, 2D:
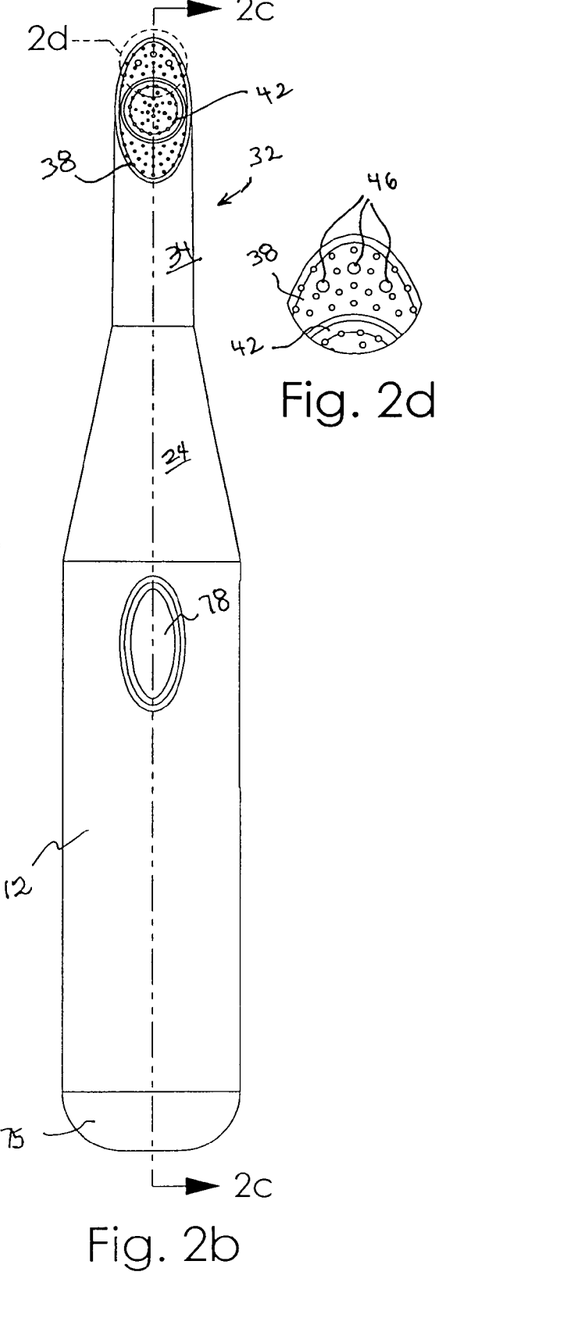
FIG. 2b is a front view of the toothbrush as in FIG. 1b.
FIG. 2d is an enlarged view of a portion of the brush head as in FIG. 2b.
Figure 2C:
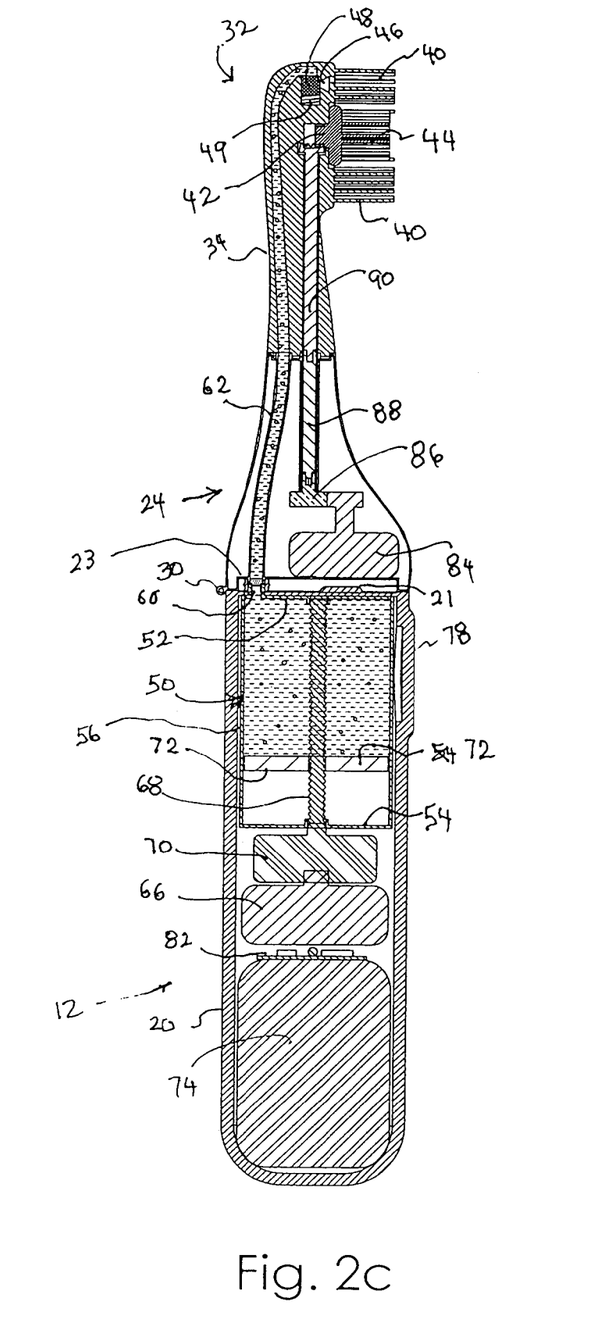
FIG. 2c is a sectional view taken along line 2c—2c of FIG. 2b.

The brush head 32 includes an arm member 34 having a first end 36 releasably coupled to the upper end 28 of the head member 24 in a snap fit relationship. The brush head 32 further includes a brush face 38 defining a plurality of apertures 46 (FIG. 2d) and having a plurality of brush face bristles 40 extending outwardly therefrom (FIGS. 2a through 2c). The brush head 32 also includes a bristle rotor 42 rotatably coupled to the brush face 38 and having a plurality of rotor bristles 44 extending outwardly therefrom (FIG. 3).

A reservoir 50 for storing a quantity of toothpaste is positioned in the interior space of the body member 12 adjacent the first end 14 thereof (FIG. 2c). The reservoir 50 includes upper 52 and lower 54 walls with a continuous side wall 56 extending therebetween (FIG. 3). The upper wall 52 of the reservoir 50 defines a refill port 60. A channel 62 extends between the reservoir refill port 60 and the brush head apertures 46 for fluid communication of toothpaste therebetween (FIG. 2c). It is understood that the channel 62 includes multiple channel segments in unitary alignment when the body member 12, head member 24 and brush head 32 are coupled together, the channel segments allowing those components to be selectively separated.

A pump assembly 64 is also positioned in the interior space of the body member 12 and is operatively coupled to the reservoir 50 for selectively urging toothpaste from the reservoir 50 into the channel 62 so as to dispense toothpaste onto the face of the brush head 32. A first motor 66 is mounted within the interior space of the brush head 32 and is electrically connected to the pump assembly 64 so as to drive the pump assembly 64 when energized to do so.

Turning more particularly to the pump assembly 64, the pump assembly 64 includes a threaded shaft 48 rotatably coupled to the first motor 66 through a gearbox 70 and extending longitudinally between the upper 52 and lower 54 walls of the reservoir 50 (FIG. 3). Further, the pump assembly 64 includes a piston 72 threadably coupled to the threaded shaft 48 such that the piston 72 moves along the shaft 68 as the shaft spins, the direction of piston movement being determined by the rotational direction of the shaft 68. The piston 72, therefore, is movable within the reservoir 50 between upper 52 and lower 54 walls. A movement of the piston 72 toward the upper wall 52 urges toothpaste into the channel 62 for movement toward the brush head apertures 46 whereas a movement of the piston 72 toward the lower wall 54 enables additional toothpaste to be deposited into the reservoir 50, as to be described in more detail later.

A rechargeable battery 74 is positioned in the bottom of the interior space of the body member 12, i.e. adjacent the second end 16. The battery 74 is electrically connected to the first motor 66 as well as to a first switch 76 that is mounted to an exterior of the body member 12. Therefore, an actuation of the first switch 76 by a user allows current to flow to the first motor 66 so as to energize the first motor 66 to drive the pump assembly 64. It should be appreciated that the first motor 66 may be a stepper motor that only operates for a predetermined amount of time when energized. With a stepper motor, only a predetermined quantity of toothpaste would be dispensed each time the first switch 76 was actuated.

It is understood that that the battery 74 may include a conventional construction that is removable from the body member 12 by first releasing a cap 75 and then releasably connected to a recharging unit. Alternatively, the body member 12 may be seated within a cavity of a recharging base 80 (FIG. 1a), the recharging base having an electrically conductive coil assembly for recharging the battery 74 (not shown). In other words, the body member 12 may simply be mounted in a recharging base 80 for recharging and storage (FIG. 1a).

The toothpaste dispensing toothbrush 10 may include simple control circuitry 82 positioned in the body member 12 electrically connected to the battery 74, first motor 66, and first switch 76 for operating the components as described above.

A second motor 84 is positioned in the head member 24 and is operatively coupled to the rotor 42. This connection includes a crown gear 86 engaged with the second motor 84 and lower 88 and upper 90 shaft segments coupled to the crown gear 86 and extending through the head member 24 and brush head 32 to the bristle rotor 42. The second motor 84 is electrically connected to the battery 74 and to a second switch 78 positioned on the exterior of the body member 12 (electrical connections not shown) such that the second motor 84 drives the bristle rotor 42 when the second motor 84 is energized by a depression of the second switch 78.

An alternative embodiment of a brush head 92 and head member 93 is shown in FIGS. 6a through 6d in which an oscillation arm 94 interconnects a second motor 96 and a bristle rotor 98. In this embodiment, the rotor 98 oscillates rotationally first in one direction and then in an opposite direction as the second motor 96 rotates and actuates the oscillator arm 94.

Figure 5A:
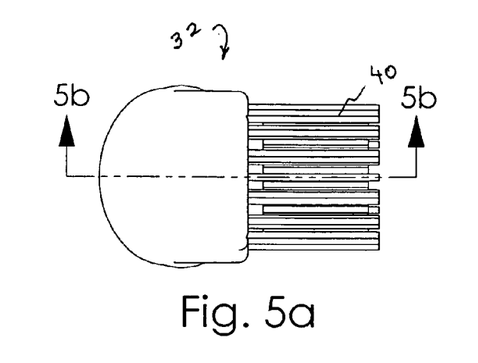
FIG. 5a is a top view of a brush head as in FIG. 1b.
Figure 5B:
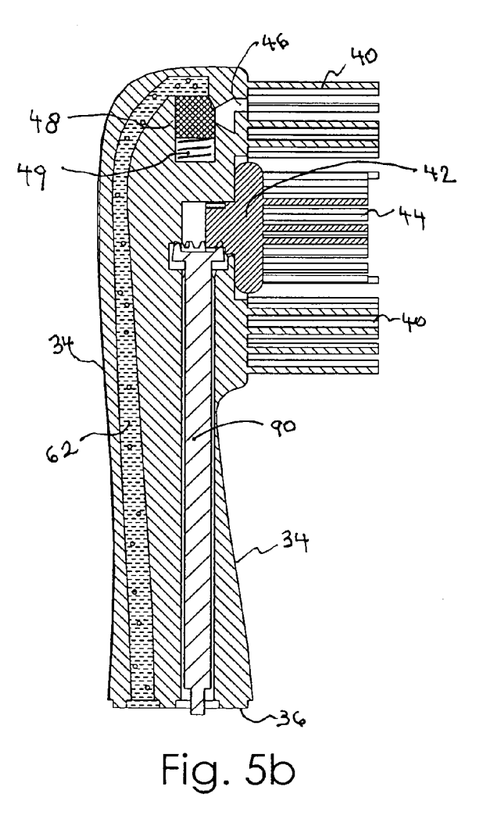
FIG. 5b is a sectional view taken along line 5b—5b of FIG. 5a with a spring-loaded valve in a closed configuration.
Figure 5C:
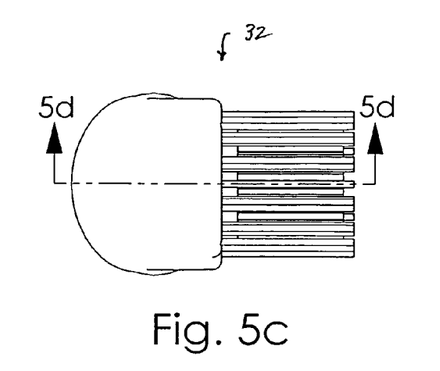
FIG. 5c is another top view of a brush head as in FIG. 1b.
Figure 5D:
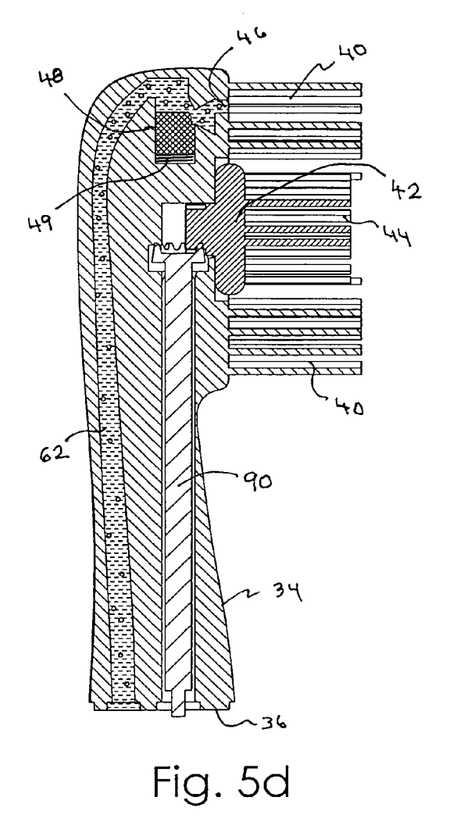
FIG. 5d is a sectional view taken along line 5d—5d of FIG. 5c with a spring-loaded valve in an open configuration.
Figure 6A:
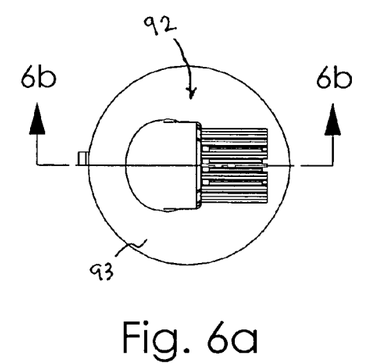
FIG. 6a is top view of a brush head and head member according to another embodiment of the invention.
Figure 6B:
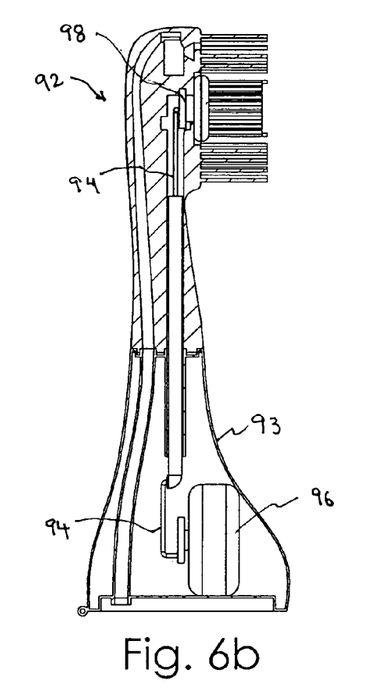
Figure 6C:
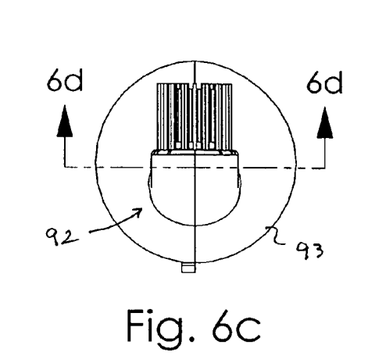
FIG. 6c is top view of a brush member and head member as in FIG. 6a taken from another angle.
Figure 6D:
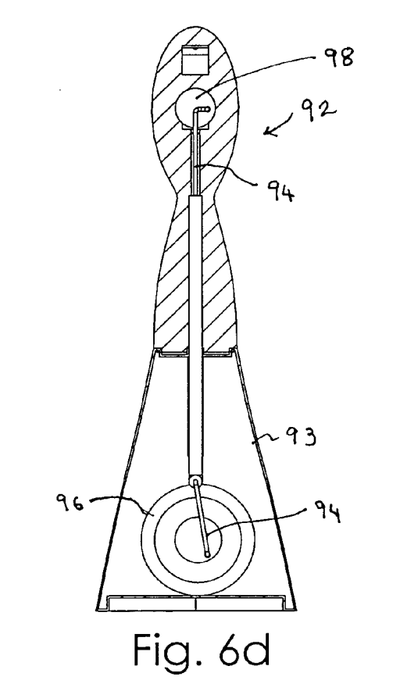
FIG. 6d is a sectional view taken along line 6d—6d of FIG. 6c.

As best shown in FIGS. 5a to 5d, the brush head 32 includes a valve 48 coupled to an end of the channel 62 and in communication with the plurality of brush head apertures 46. The valve 48 is operable between an open configuration in which toothpaste flowing through the channel is dispensed onto the face 38 of the brush head 32 (FIG. 5d) and a closed configuration preventing dispensing of toothpaste (FIG. 5b). The valve 48 includes a compression spring 49 such that the valve 48 compresses the spring 49 and is urged to the open configuration (FIG. 5d) when toothpaste is being urged through the channel 62 upon operation of the pump assembly 64 and the valve 48 is normally urged to the closed configuration (FIG. 5b) by the natural spring bias when toothpaste is not being urged through the channel 62.

The body member 12 includes a side wall 20 defining a window 22 proximate the reservoir 50 and that extends substantially the longitudinal extent thereof. Preferably, the reservoir 50 is constructed of a transparent material such that the level of toothpaste remaining in the reservoir 50 may be observed by a user through the window 22.

Referring to FIGS. 3 and 4b, the top wall 18 of the body member 12 defines an inlet port 23 aligned with the corresponding refill port 60 in the upper wall 52 of the reservoir 50 for fluid communication therewith. The inlet port 23 includes a threaded configuration complementary to a configuration of conventional toothpaste container nozzles such that a toothpaste container may be releasably coupled with the inlet port 23 for depositing toothpaste into the storage reservoir 50. It should be observed that the inlet port 23 is aligned with the channel 62 which extends through the head member 24 such that the channel 62 nests in the inlet port 23 when the head member 24 is in the closed configuration (FIG. 2c). In addition, a pump reversal button 21 is positioned on the body member top wall 18 and electrically connected to the first motor 66. Actuation of the pump reversal button 21 causes the first motor 66 to operate the pump assembly shaft 68 in a direction that causes the piston 72 to move toward the lower wall 54 of the reservoir 50 so as to make room for an addition of toothpaste into the reservoir 50.

Figure 4A:
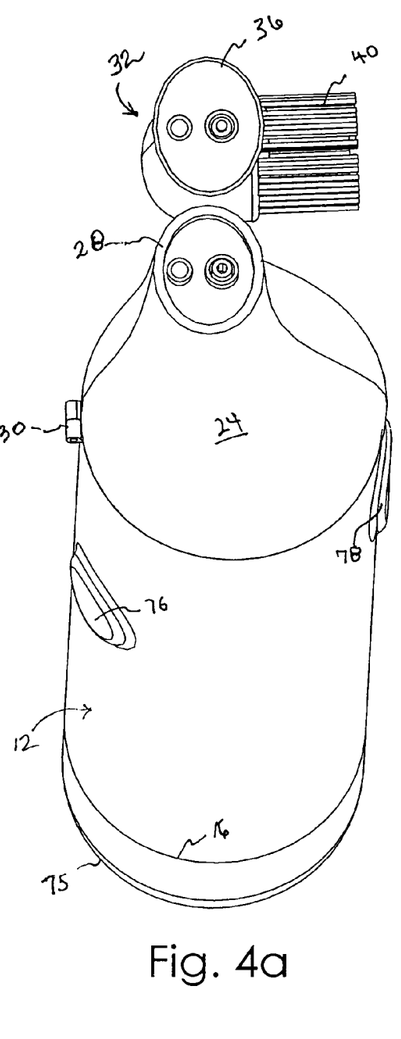
FIG. 4a is an elevated perspective view of the toothbrush as in FIG. 1b with the head member in a closed configuration and the brush member released.
Figure 4B:
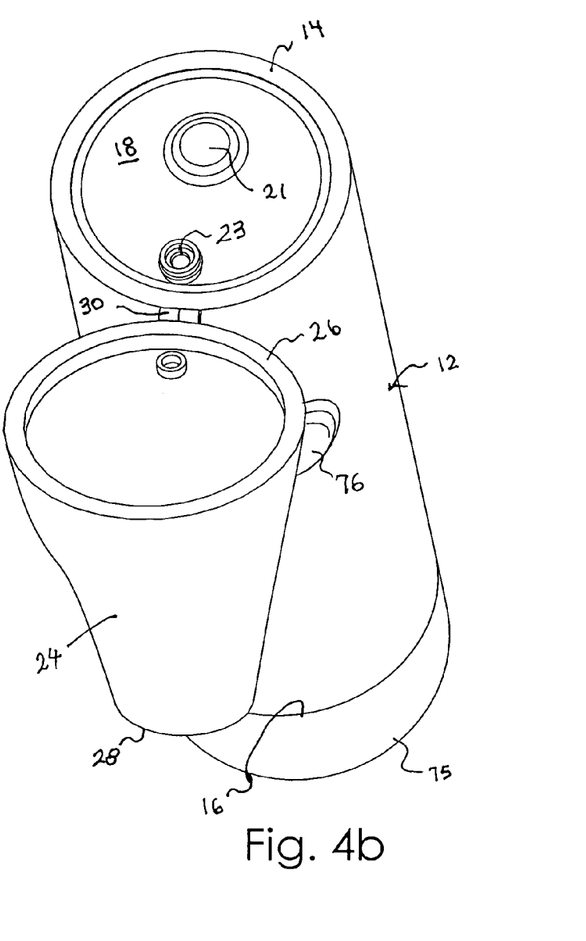
FIG. 4b is an elevated perspective view of the toothbrush as in FIG. 4a with the head member in an open configuration and with the brush head completely removed.

FIG. 4a further illustrates the alignment of portions of the channel 62 that extend through the head member 24 and brush head 32. FIG. 4a also shows alignment of segments of the shaft 68 that connects the second motor 84 housed in the head member 24 with the bristle rotor 42 in the brush head 32. Preferably, the shaft segments are releasably coupled together in a male/female configuration.

Preferably, a portion of the bristles, such as the rotor bristles, are constructed of a colored material that fades as the brush is used so as to indicate to a user when the brush head should be replaced. Another desirable feature is to include a timer circuit as a component of the control circuitry 82 (FIG. 3) that would either operate the second motor 84 and bristle rotor 42 for a predetermined amount of time following actuation of the second switch 78 or to energize a buzzer after a predetermined time. The timer feature aids in encouraging an appropriate amount of brushing by the user.

In use, the head member 24 may be pivoted to an open configuration and toothpaste may be deposited into the reservoir 50 through the inlet port 23 which is connected to the reservoir refill port 60 (FIGS. 2c and 4b). The reservoir 50 may be later refilled in the same manner and pressing the pump reversal button 21 allows the piston 72 within the reservoir 50 to move in a downward direction to make room for the toothpaste. With the head member 24 returned to a closed configuration and the brush head 32 coupled thereto (FIG. 1b), a user may depress the first switch 76 to activate the internal pump assembly 64 to urge toothpaste from the reservoir 50 through the channel 62 and valve 48 onto the face of the brush head 32 (FIG. 2c). The second switch 78 may then be depressed to energize the second motor 84 to operate the brush head rotor 42 for brushing a user's teeth. The window 22 in the body member 12 may be monitored to determine when more toothpaste needs to be deposited into the reservoir 50.

It is understood that while certain forms of this invention have been illustrated and described, it is not limited thereto except insofar as such limitations are included in the following claims and allowable functional equivalents thereof.

Having thus described the invention, what is claimed as new and desired to be secured by Letters Patent is as follows:

1. A toothpaste dispensing automatic toothbrush, comprising:
    a body member having opposed first and second ends and defining an interior space;
    a head member having a lower end coupled to said first end of said body member and having an upper end;
    a brush head releasably coupled to said head member upper end and having a plurality of brush head bristles extending outwardly therefrom, said brush head having a hollow configuration and defining a plurality of apertures proximate said plurality of brush head bristles;
    a reservoir positioned in said interior space adjacent said first end for storing toothpaste, said reservoir having upper and lower walls;
    a channel interconnecting said reservoir and said plurality of apertures;
    a piston mounted in said reservoir for movement between said upper and lower walls, whereby a piston movement toward said upper wall urges said toothpaste through said channel to said plurality of apertures in said brush head;
    a battery positioned in said interior space;
    a first motor positioned in said interior space and operatively coupled to said piston for driving said piston; and
    a first switch mounted on said body member and electrically connected to said battery and to said first motor for selectively energizing said first motor, whereby to dispense said toothpaste through said brush head apertures and onto said brush head bristles the brush head includes a rotor having a plurality of rotor bristles extending outwardly therefrom, the toothbrush further comprising a second motor positioned in the head member and operatively connected to the rotor; and a second switch mounted on the body member and electrically connected to the battery and to the second motor for selectively energizing the second motor, whereby to selectively rotate the plurality of rotor bristles.

2. The toothbrush as in claim 1 wherein said first motor is a stepper motor that is energized for a predetermined amount of time upon actuation of said first switch.

3. The toothbrush as in claim 1 further comprising a threaded shaft rotatably coupled to said first motor and extending longitudinally between said upper and lower walls of said reservoir, said piston being threadably coupled to said shaft such that said piston moves longitudinally along said shaft according to the rotational direction of said shaft.

4. The toothbrush as in claim 1 wherein said battery is rechargeable.

5. The toothbrush as in claim 4 further comprising a base unit having means for recharging said battery.

6. The toothbrush as in claim 1 further comprising timer means for automatically interrupting current to said second motor when said second motor has been energized for a predetermined amount of time.

7. The toothbrush as in claim 1 wherein said rotor bristles are constructed of a colored material that gradually fades upon repeated use.

8. The toothbrush as in claim 1 further comprising a third switch mounted atop said first end of said body portion and electrically connected to said first motor for selectably reversing the rotational direction of said first motor.

9. The toothbrush as in claim 1 wherein said body portion defines a window adjacent said first end such that a level of toothpaste contained in said reservoir is observable.

10. The toothbrush as in claim 1 further comprising a spring-loaded valve connected to an end of said channel adjacent said plurality of apertures, said valve being operable between an open configuration when said toothpaste is being urged through said channel and a closed configuration when said toothpaste is not being urged through said channel, whereby said toothpaste does not accumulate or dry up at said end of said channel.

11. The toothbrush as in claim 1 wherein said lower end of said head member is pivotally coupled to said first end of said body member such that said head member is selectively movable between open and closed configurations.

12. The toothbrush as in claim 11 further comprising an inlet port extending through said first end of said body member in communication with said reservoir for receiving additional toothpaste into said reservoir when said head member is in said open configuration.

13. A toothpaste dispensing automatic toothbrush, comprising:
- a body member having opposed first and second ends and defining an interior space;
- a head member having a lower end coupled to said first end of said body member and having an upper end;
- a brush head releasably coupled to said head member upper end, said brush head having a hollow configuration and defining a plurality of apertures, said brush head further comprising:
  - a plurality of brush head bristles extending outwardly therefrom and positioned proximate said plurality of apertures;
  - a rotor having a plurality of rotor bristles extending outwardly therefrom;
- a reservoir positioned in said interior space adjacent said first end for storing toothpaste, said reservoir having upper and lower walls;
- a battery positioned in said interior space;
- a channel interconnecting said reservoir and said plurality of apertures;
- a pump assembly operatively coupled to said reservoir for selectively urging said toothpaste into said channel;
- a first motor coupled to said pump assembly for driving said pump assembly when energized;
- a first switch mounted on said body member and electrically connected to said battery and to said first motor for selectively energizing said first motor, whereby to dispense said toothpaste through said brush head apertures and onto said brush head bristles;
- a second motor positioned in said head member and operatively coupled to said rotor; and
- a second switch mounted on said body member and electrically connected to said battery and to said second motor for selectively energizing said second motor, whereby to selectively cause movement of said plurality of rotor bristles.

14. The toothbrush as in claim 13 wherein said pump assembly includes:
- a threaded shaft rotatably coupled to said first motor and extending longitudinally between said upper and lower walls of said reservoir;
- a piston threadably coupled to said shaft for longitudinal movement therealong between said upper and lower walls of said reservoir according to the rotational direction of said shaft, whereby said toothpaste is urged into said channel when said piston is moved toward said upper wall of said reservoir.

15. The toothbrush as in claim 13 further comprising a third switch mounted atop said first end of said body portion and electrically connected to said first motor for selectably reversing the rotational direction of said first motor.

16. The toothbrush as in claim 15 wherein said lower end of said head member is pivotally coupled to said first end of said body member such that said head member is selectively movable between open and closed configurations.

17. The toothbrush as in claim 16 further comprising an inlet port extending through said first end of said body member in communication with said reservoir for receiving additional toothpaste into said reservoir when said head member is in said open configuration.

18. The toothbrush as in claim 13 further comprising a spring-loaded valve connected to an end of said channel adjacent said plurality of apertures, said valve being operable between an open configuration when said toothpaste is being urged through said channel and a closed configuration when said toothpaste is not being urged through said channel, whereby said toothpaste does not accumulate or dry up at said end of said channel.

19. The toothbrush as in claim 13 wherein said body portion defines a window adjacent said first end such that a level of toothpaste contained in said reservoir is observable.

* * * * *